United States Patent [19]
Axelrod et al.

[11] Patent Number: 4,959,481
[45] Date of Patent: Sep. 25, 1990

[54] FLAME RETARDANT COMPOUNDS AND THERMOPLASTIC COMPOSITIONS CONTAINING THE SAME

[75] Inventors: Robert J. Axelrod, Glenmont, N.Y.; Donald B. G. Jaquiss, Pittsfield, Mass.; John A. Tyrell, Mt. Vernon, Ind.

[73] Assignee: General Electric Company, Selkirk, N.Y.

[21] Appl. No.: 189,970

[22] Filed: May 4, 1988

Related U.S. Application Data

[62] Division of Ser. No. 892,344, Aug. 1, 1986, Pat. No. 4,743,637.

[51] Int. Cl.⁵ .................. C07D 209/02; C07D 209/48
[52] U.S. Cl. .................................................... 548/462
[58] Field of Search ........................................ 548/462

[56] References Cited

U.S. PATENT DOCUMENTS

| | | | |
|---|---|---|---|
| 3,855,277 | 12/1974 | Fox | 529/409 |
| 3,868,388 | 2/1975 | Dotson, Jr. et al. | 548/462 |
| 3,915,930 | 10/1975 | Dotson, Jr., et al. | 548/462 |
| 4,098,704 | 7/1978 | Sandler | 252/8.6 |
| 4,208,489 | 6/1980 | Schmidt et al. | 525/146 |
| 4,294,944 | 10/1981 | Newkirk et al. | 525/423 |
| 4,312,966 | 1/1982 | Newkirk et al. | 525/425 |
| 4,374,220 | 2/1983 | Sonnenberg | 524/94 |
| 4,397,977 | 8/1983 | Sandler | 524/288 |
| 4,433,088 | 2/1984 | Haaf et al. | 524/153 |
| 4,456,720 | 6/1984 | Abolins et al. | 524/176 |
| 4,506,047 | 3/1985 | Witman et al. | 524/89 |
| 4,526,917 | 7/1985 | Axelrod | 524/141 |
| 4,535,170 | 8/1985 | Sonnenberg | 548/462 |
| 4,743,637 | 5/1988 | Axelrod et al. | 524/94 |
| 4,769,475 | 9/1988 | Sasaki et al. | 548/462 |

FOREIGN PATENT DOCUMENTS

0044703 1/1982 European Pat. Off.
1815404 6/1970 Fed. Rep. of Germany ...... 548/462

Primary Examiner—Kriellion Morgan
Attorney, Agent, or Firm—Hedman, Gibson, Costigan & Hoare

[57] ABSTRACT

Novel flame retardant agents comprise polyalkylene oxides or a derivative thereof and end-capped with brominated phthalimide groups, and have the general formulae

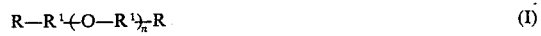

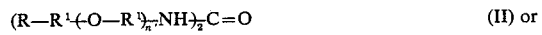

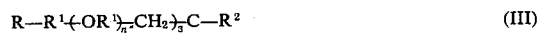

wherein R is

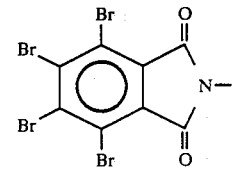

$R^1$ is alkylene of from about 2 to about 6 carbon atoms; $R^1$ is alkyl of from about 1 to about 6 carbon atoms; n is from about 4 to about 40; n' is from about 3 to about 15; and n" is from about 1 to about 10. Thermoplastic compositions, for example, polyphenylene ether compositions, rendered flame retardant with the novel compounds have a high resistance to additive vaporization and surface liquid exudation as well as desirable high flow characteristics.

36 Claims, No Drawings

FLAME RETARDANT COMPOUNDS AND THERMOPLASTIC COMPOSITIONS CONTAINING THE SAME

This is a divisional of application Ser. No. 892,344 filed Aug. 1, 1986 now U.S. Pat. No. 4,743,637.

This invention relates to new and novel flame retardant compounds and in particular to thermoplastic compositions containing them. More particularly, it is concerned with novel low polymers of polyalkylene oxides or derivatives derived therefrom end-capped with brominated phthalimide groups and flame retardant combinations thereof with normally flammable thermoplastic resins.

BACKGROUND OF THE INVENTION

The use of certain additives for the purpose of reducing the flammability of various thermoplastic polymers is well known to those skilled in the art. Flame retardant thermoplastic compositions are desired for many fields of use, such as in home construction, automobile and aircraft manufacture, packaging, electrical equipment, and the like.

Many thermoplastics ignite at relatively low temperatures and others have high ignition temperatures. Among the former can be mentioned polystyrene, polyethylene, cellulose esters, e.g., cellulose acetate and cellulose nitrate, and polyesters, e.g., poly(ethylene terephthalate). These resins are generally regarded to be highly flammable. On the other hand, some thermoplastics, such as the aromatic polycarbonates, polyphenylene ethers, polysulfones, polybenzimidazoles, polyamides, and the like ignite at temperatures far in excess of the others, e.g., at above 700° F., or so. Although not considered to be highly flammable, they still are potentially dangerous unless rendered flame retardant. For convenience, all such resins will be classified herein as "normally flammable" because, although there is a high ignition temperature, a polycarbonate, for example, can support combustion beyond 20 seconds after ignition and subsequent removal of the igniting source and, in particular, burning is seen in thin sections.

It is therefore desirable to provide compositions which will not support combustion beyond a few seconds, both for the highly flammable resins, but in particular, even for those of high ignition temperature.

In the art of rendering thermoplastic resins flame retardant many materials have been used as flame retardant additives. Many of the additives are halogen containing compounds and these have been fairly successful in accomplishing the desired result, but at some sacrifice in physical properties in parts molded from the compositions. Often, however, increasing the amounts of conventional halogenated flame retardant compounds has an undesirable over-plasticizing effect on the normally rigid molded parts. In addition, especially with the high ignition temperature thermoplastics, a point is reached above which increased amounts of the known flame-retardant compounds do not improve the flame-out property of the composition. Finally, most of the conventional halogenated flame retardant compounds, in addition to lessening the desirable properties of the base polymer, are somewhat volatile and "plate out" on the surface of the molded pieces. This problem is especially aggravated in the case of polyesters and the high ignition point thermoplastics such as polyphenylene ether resins, alone, or in further combination with high impact rubber-modified polystyrene resins (HIPS), which ordinarily are processed at temperatures above about 200° C., at which point the conventional halogenated materials tend to plate out.

As representative of the present state of the art, Fox, U.S. Pat. No. 3,855,277, discloses flame retardant agents comprising low molecular weight polymers of a carbonate of a halogenated dihydric phenol alone or in combination with an inorganic or organic antimony-containing compound.

Sandler, U.S. Pat. No. 4,098,704, discloses that poly(alkylene oxides) end-capped with tetrahalophthalate ester or amide groups are useful to provide textiles with a flame-retardant finish. In one example, tetrabromophthalic anhydride is reacted with a diprimary amine end-capped polypropylene oxide, and a half acid-amide end-capped product is produced. However, the patent provides no teaching that any of the compounds will function efficiently as non-migratory internal flame retardants in thermoplastics.

Newkirk et al., U.S. Pat. Nos. 4,294,944 and 4,312,966, disclose that the reaction products of polyoxyalkylene compounds and halogenated aromatic diacids and anhydrides function as flame-retardant antistatic additives for polymer fibers. However, this patent makes it desirable to use the additives in the form of a coating on the surface of the fiber to provide a softening effect, or to take advantage of their migration to the surface to provide anti-static effects, and this would not be desirable in three dimensional molded articles, as mentioned above.

Sandler, U.S. Pat. No. 4,397,977, discloses a flame retardant composition comprising a tetrahalophthalate plasticizer and a halogenated resin, in which the plasticizer appears to have been made by reacting a tetrahalophthalate with a polyoxyalkylene compound or amino derivative thereof. In any event, the compounds are di-esters or half-acid esters, half-acid amides or half-ester amides. There is no disclosure of phthalimido end-capped units and no teaching that the plasticizers would be non-migratory.

Halogenated flame retardant agents are also disclosed in Haaf et al., U.S. Pat. No. 4,433,088, and Abolins, U.S. Pat No. 4,456,720. Haaf et al. disclose compositions using an aromatic phosphate compound such as isopropylated triphenyl phosphate and an adhesion promoting agent selected from a polyolefin glycol or a polyamide wherein the composition is essentially free of a polyolefin. The Abolins patent discloses that using halogenated organic compounds with boron containing salts and esters which are stable at 250°–300° C. improve the flame retardant properties of thermoplastic compositions.

Admixtures of triaryl phosphates and various thermoplastic resins are disclosed in Axelrod, U.S. Pat. No. 4,526,917, to render thermoplastic compositions flame retardant.

However, halogenated and/or phosphorus-containing flame retardant agents used in the aforementioned references are still not entirely satisfactory, especially when incorporated into thermoplastic compositions, particularly thermoplastic compositions composed of polyphenylene ethers and high impact polystyrene. More specifically, triaryl phosphate based flame retardant agents, may sometimes adversely affect the environmental stress crack resistance of thermoplastic resins, since they also form a liquid deposit on injection molds. Efforts to reduce the volatility of the phosphate containing flame retardants by increasing molecular weight have not always been successful because flame retardancy tends to be decreased.

With respect to adding halogenated materials such as brominated polycarbonates and brominated esters, as well as brominated polystyrene to normally flammable thermoplastic compositions to render the same flame retardant, such flame retardants have the drawback of being generally incompatible with the resins, especially° polyphenylene ether resins, and they thereby adversely affect the physical and thermal resistance characteristics of the blended composition.

It has now been discovered that low molecular weight polyalkylene ether polymers and derivatives thereof can be provided with tetrabromophthalimide end groups, e.g., by reacting amino-terminated such polymers with tetrabromophthalic anhydride, and that these are very useful additives to render polymers flame retardant. Furthermore, the softening points of these low molecular weight products can be tailored to suit a particular resin system into which they are to be incorporated.

Such products can be used alone to render normally flammable thermoplastic compositions flame retardant. They may also be used in combination with synergists, such as phosphorous compounds, but particularly with inorganic or organic antimony compounds.

By way of illustration, a low molecular weight tetrabromophthalimide end-capped poly(ethylene oxide) or poly(propylene oxide) or a derivative thereof having a molecular weight of between about 400 and about 2000 and a bromine content of between about 5 and 55 percent by weight, and melting at less than 200° C., is uniquely advantageous in rendering a polyphenylene ether-styrene resin composition flame retardant. Other polymers rendered flame retardant include poly(ethylene terephthalate), poly(butylene terephthalate), poly(bisphenol A carbonate), and an acrylonitrilebutadienestyrene terpolymer.

Such compositions, which may also contain antimony compounds, are "self-extinguishing" and meet the stringent requirements of the Underwriters Laboratories Bulletin 94 flame test, without loss of ultimate physical properties and without plate-out of the additive or volatilization during injection molding.

The additives also possess a significant plasticization effect, with very little tendency to over-plasticize, and this overcomes a major drawback in the present state of the art. Flame retardancy is as good or better than with triaryl phosphates without volatility problems, and as good as that of the brominated additives, but without incompatibility problems often observed.

It is a principal object of this invention, therefore, to provide a class of highly efficient, novel, low molecular weight polybrominated phthalimide end-capped poly(alkylene oxides) for use as flame retardant agents.

Another object of the invention is to provide improved flame retardant polymer compositions containing such low molecular weight flame retardant additives.

Yet a further object of the invention is to provide flame retardant compositions from which the additive does not volatize during, or remain on the surface after, molding.

Still another object of the invention is to provide plasticized, flame retardant molding compositions.

Other objects and advantages of the invention will become apparent from the following detailed description.

DESCRIPTION OF THE INVENTION

According to this invention there are provided flame retardant compounds comprising a polyalkylene oxide or derivative thereof end-capped with brominated phthalimide groups and having the formula

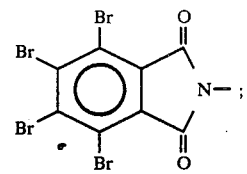

$R^1$ is selected from alkylene of from about 2 to about 6 carbon atoms, preferably, ethylene or propylene; $R^2$ is alkyl of from about 1 to about 6 carbon atoms; n is from about 4 to about 40, preferably about 5 to about 33; n' is from about 3 to about 15, preferably about 4 to about 8, especially preferably from about 5 to about 6, and n" is from about 1 to about 10, preferably about 1.5 to about 2.5.

The present invention also contemplates flame retardant thermoplastic compositions comprising:
(a) a normally flammable thermoplastic resin; and
(b) a flame retardant amount of either
  (i) a polyalkylene oxide compound or derivative thereof end-capped with brominated phthalimide groups of formulae (I), (II) or (III) above; or
  (ii) a combination of said compound (i) and an inorganic or organic antimony-containing compound.

In preferred features, compounds will be selected in which $R^1$ is a

group, and especially

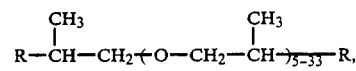

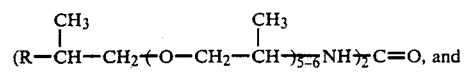

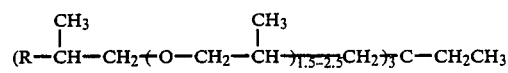

wherein R is as above defined.

In other preferred features, the normally flammable thermoplastic resin is selected from:
a polyphenylene ether or a mixture thereof with a polystyrene resin;
a polymerization product of a vinyl monomer;
a polymerization product of an olefin monomer;
a polymerization product of an acrylic or methacrylic monomer;
a polymerization product of a diene monomer;
a polyamide;
a cellulose ester;
a polyester;
an aromatic polycarbonate; or
a mixture of at least two of the foregoing.

Special mention is made of a preferred embodiment in which:

the polyphenylene ether is a poly(2,6-disubstituted-1,4-phenylene ether) or a poly(2,6-dimethyl-1,4-phenylene-co-2,3,6-trimethyl-1,4-phenylene ether) or a mixture of either or both of the foregoing;

the aromatic polycarbonate is poly(bisphenol-A carbonate);

the polyester is poly(1,4-butylene terephthalate); and the polymerization product of an allyl monomer is a polybutadiene or a rubbery copolymer of styrene and butadiene with acrylonitrile and styrene.

DETAILED DESCRIPTION OF THE INVENTION

When used herein, the term "flame retardant" is used in the sense that the resistance to combustibility of the composition is significantly increased in comparison with control samples. A suitable direct measurement of combustibility is the Oxygen Index Test or LOI (Limiting Oxygen Index). This test measures a product's combustibility based on the oxygen content of the combustion atmosphere. Appropriate specimens are placed in a combustion chimney and the oxygen is reduced stepwise until the material no longer supports a flame. The LOI is defined as the percent oxygen times 100 divided by the sum of the percentages of nitrogen and oxygen in the gas used to burn the material under test. Further details of the Oxygen Index Test are found in ASTM test method D-2863. The compositions of this invention which contain flame retardant additives of the specified types in the specified amounts have a substantially higher oxygen index and thus are much less combustible than the controls.

Another useful criterion for measuring flame retardancy is to determine if the composition qualifies to be designated "non-burning" or "self-extinguishing" by the tests set forth in Underwriters' Laboratories bulletin No. 94. In such tests if the specimens extinguish themselves within 5 to 30 seconds, after two 10 second ignitions in an open flame, flame retardancy has been established.

The term "normally flammable thermoplastic resin" includes those types generally described above, including those which ignite at relatively low and at relatively high temperatures. It is intended to exclude resins which are not normally flammable, because they inherently contain, or are modified to contain, elements, such as halogen, phosphorus, large quantities of nitrogen and the like, which render them flame retardant. Illustrative of resins which are not "normally flammable" and therefore not included as the primary resin component (a) in the compositions of the present invention are polyvinyl chloride, polytetrafluoroethylene, chlorinated polyethylene, polyesters of halogenated anhydrides, high molecular weight halogenated aromatic polycarbonates, and the like.

By way of illustration, the normally flammable thermoplastic resin can be selected from a polymerization product of a vinyl monomer, e.g., a vinyl aromatic compound, such as styrene, vinyl toluene, vinyl naphthalene, vinyl benzene, or mixtures thereof, vinyl esters, e.g., vinyl acetate or vinyl butyrate, methylene methyl malonate, a polymerization product of an olefinic monomer, such as ethylene, propylene, 1- and 2-butene, 1-decene, or a diene, such as butadiene or isoprene, and the like, including interpolymerization products thereof with vinyl monomers, e.g., butadiene styrene copolymers, and terpolymers with alkenyl cyanides, e.g., acrylonitrile, a polymerization product of an acrylic or methacrylic monomer, e.g., acrylic acid, methyl acrylate, ethyl acrylate, n-propyl acrylate, isopropyl acrylate, n-butyl acrylate, t-butyl acrylate, hexyl acrylate and the corresponding alkyl methacrylates, polymerization products of allyl monomers, such as methyl allyl ketone, ethyl vinyl ether, diallyl ether, N-allyl caprolactam. N-allyl acrylamide, a polymerization product of an unsaturated ketone, e.g., methyl vinyl ketone, and the like, a polyamide, such as adipic acid-hexamethylenediamine reaction products, cellulosic esters, such as cellulose acetate, cellulose butyrate, cellulose nitrate; aromatic polycarbonates, such as phosgene-bisphenol-A reaction products; polyphenylene ethers), such as poly(2,6-dimethyl-1,4-phenylene ether), poly(2,6-dimethyl-1,4-phenylene-co-2,3,6-trimethyl-1,4-phenylene ether) and poly(2,6-diphenyl-1,4-phenylene ether) alone and in combination with styrene resins; the polysulfones, such as polyphenylene sulfone; polybenzimidazoles; and polyesters, such as wholly aromatic polyesters, e.g., hydroquinone-terephthaloyl chloride reaction products; wholly aliphatic polyesters, and poly(alkylene iso and terephthalates), such as the highly polymerized reaction products of an ester of the corresponding phthalic acid with a glycol, such as described in U.S. Pat. Nos. 2,465,319 and 3,047,539, and elsewhere.

In especially preferred embodiments of this invention, the normally flammable thermoplastic resin component will be a polyphenylene ether alone or in combination with a styrene resin, an aromatic polycarbonate, e.g., poly(bisphenol-A carbonate); a polyester, and particularly a poly(alkylene terephthalate, isophthalate or mixed isophthalateterephthalate), the alkylene groups containing from 2 to 10 carbon atoms, e.g., poly(ethylene terephthalate) or poly(1,4-butylene terephthalate); an interpolymerization product is a diene rubber, an alkenyl cyanide and a vinyl aromatic compound, e.g., a product of a butadiene or a rubbery copolymer of styrene and butadiene, interpolymerized with acrylonitrile and styrene. All such resins are widely available commercially and can be prepared by procedures known by those skilled in the art.

The low molecular weight polymers of this invention should be selected preferably to provide plasticization as well as flame retardancy. The materials may vary in molecular weight, percent bromine content and monomer structure. For an optimum balance of flame retardancy and plasticization properties, it appears that minimizing the polyalkylene chain length is desirable, so long as the glass transition temperature is not at the same time increased. In any event, plastization is easily followed by flow channel measurements and flammability is likewise followed easily by standard flammability tests, e.g., by the Underwriters Laboratory Bulletin UL 94 Test.

The low molecular weight compounds of this invention can be prepared by reacting a polybromophthalic anhydride with a poly(alkylene oxide) or a derivative thereof terminated with primary amine groups. The alkylene groups can be alkylene of up to 6 carbon atoms, such as ethylene or propylene, butylene, pentylene, hexylene, and the like, groups, and the polyether groups can be linear or branched. The molecular weight of the product will be a function of the number of repeating units in the polyether, typically, 4–8 and 33 units are commercially available, although a wide range of molecular weights can be used.

Polyoxypropylene amines are sold under the Trademark Jeffamines by Texaco Chemical Company with a letter and number as part of the mark, such as Jeffamine D-400 ®. The letter "D" denotes the compound has two primary amine groups per molecule "T" denotes three amino groups per molecule. The number denotes the average molecular weight.

To prepare the compounds of formula (II) a corresponding primary amine end-capped polyalkyleneoxide urea can be reacted with tetrabromophthalic anhydride. Such ureas are available by reacting polyoxyalkylene amines with phosgene or an equivalent such urea, diphenyl carbonate, and the like and are available from Texaco Chemical Company, under the trade name DU 700 ®.

As has been mentioned, it is a preferred feature of this invention to use the low molecular weight (additive (b)(i)) in combination with a synergist. Suitable synergists include inorganic and organic antimony compounds. Such compounds are widely available or can be made in known ways. The type of antimony compound used is not critical, being a choice primarily based on economics. For example, as inorganic compounds, there can be used antimony oxide, $(Sb_2O_3)$; antimony phosphate; $KSb(OH)$; $NH_4SbF_6$; $SbS_3$; and the like. A wide variety of organic antimony compounds can also be used, such as antimony esters with organic acids; cyclic alkyl antimonites; aryl antimonic acids, and the like. Illustrative of the organic antimony compounds, including inorganic salts of compounds are: KSb tartrate; Sb caproate; $Sb(OCH_2CH_3)_3$; $Sb(OCH(CH_2)CH_2CH_3)_3$; Sb polymethylene glycolate; triphenyl antimony; and the like. Especially preferred is antimony oxide.

The amount of low molecular weight poly ether or derivative thereof end-capped with halogenated phthalimide used as a flame retardant additive is not critical to the invention, so only as it is present in a minor proportion based on said compositions—major proportions are uneconomical and may detract from physical properties—but at least sufficient to render the thermoplastic resin flame retardant, non-burning or self-extinguishing, as the case may be. Those skilled in the art are well aware that the amount will vary with the nature of the flammable thermoplastic resin and the relative efficiency of the additive. In general, however, the amount of additive will be from 0.5 to 50 parts by weight per 100 parts by weight of resinous component (a), with the lesser amounts providing flame retardancy, and the higher amounts being used for self-extinguishing properties. A preferred range will be from about 1.0 to 30 parts and an especially preferred range will be from about 5 to about 25 parts of additive per 100 parts of resinous component (a). Smaller amounts of compounds highly concentrated in bromine will be sufficient, e.g., where n or n' is 7, larger amounts will be needed than where n or n' is 3 or 4. The amount of antimony compound can vary over a fairly wide range, but, in general, there is used from about 0.5 to about 20 parts by weight, expressed as antimony oxide, per 100 parts of thermoplastic resinous component (a), and preferably from about 1 to about 10 parts by weight of antimony oxide. Corresponding molar equivalent amounts of the other antimony compounds can be used. In the combinations of antimony and the poly(ether-halogenated phthalimides) contemplated by the invention, the weight ratio in the combination can vary widely, but it is preferred to use from about 0.1 to 1.0 parts of antimony compound for each 1.0 part by weight of the low polymer additive component.

It is, also regarded to be among the features of this invention to include in the compositions, other ingredients, such as fillers, reinforcements, mold release agents, pigments, stabilizers, nucleating agents, and the like, in conventional amounts for their conventionally employed purposes.

The manner of adding the flame retardant additives to the thermoplastic resin and, optionally, any reinforcing agent, is not critical; is conventional; and will be obvious to those skilled in the art. Preferably, however, each ingredient is added as part of a blend premix and the latter is mixed, e.g., by passage through an extruder, or by fluxing on a mill, at a temperature dependent on the needs of the particular compositions. The mixed composition can be cooled and cut up into molding granules and molded or extruded or formed into any desired shape.

It is to be understood that the compositions of the invention can be used in many different ultimate shapes. For example, they may be molded into three-dimensional articles, or formed into films, or shaped into fibers, by conventional techniques.

DESCRIPTION OF THE PREFERRED EMBODIMENTS

The following examples illustrate the preparation of certain compounds and compositions within the scope of this invention. They are not to be construed to limit the scope of the invention in any manner whatsoever.

EXAMPLE 1

To a 3-necked round bottom flask equipped with an overhead stirrer and a Dean Stark Trap is added tetrabromophthalic anhydride and polyoxypropylene diamine (a product produced by Texaco Chemical Co. under the Tradename Jeffamine ® D 2000) in a 2:1 molar ratio. The flask has a volume of approximately 3 cc/g of reactant to allow for foaming. The flask containing the reactants is placed in an oil bath under a slight nitrogen atmosphere. The oil bath is heated to about 160°–180° C. and stirring is commenced as soon as the solids have sufficiently dissolved. A major portion of the water is removed during the first 30 minutes of heating and the reaction is stirred for a total of about 2 to 3 hours to completion. The product is cooled and is a waxy material. It is used, as such. The bromine content is 22% by weight.

EXAMPLE 2

The procedure of Example 1 is repeated, substituting a polyoxypropylene diamine with a molecular weight of about 400 (Jeffamine ® D 400). The product melts at 146° C. and has a bromine content of about 50% by weight.

EXAMPLE 3

The procedure of Example 1 is repeated, substituting a poly(oxyethylene) diamine having a molecular weight of about 900 (Jeffamine ® ED 900). The product has a melting point of about 80° C. and has a bromine content of about 35% by weight.

EXAMPLE 4

The procedure of Example 1 is repeated, substituting a di(aminopolyoxypropylene) urea with a molecular weight of about 700 (Jeffamine® DU 700). The product melts at about 125° C. and has a bromine content of about 37% by weight.

EXAMPLE 5

The procedure of Example 1 is repeated, substituting a polyoxypropylene triamine having a molecular weight of about 440 (Jeffamine® T 403) and the general formula:

$$CH_3CH_2C\begin{array}{l}-CH_2{+}OCH_2CH(CH_3){\overline{)_r}}NH_2\\-CH_2{+}OCH_2CH(CH_3){\overline{)_s}}NH_2\\-CH_2{+}OCH_2CH(CH_3){\overline{)_t}}NH_2\end{array}$$

wherein r+s+t is about 5.3. The product melts at about 80° C. and has a bromine content of about 53% by weight.

EXAMPLE 6

A composition is prepared comprising 50 parts by weight of poly(2,6-dimethyl-1,4-phenylene ether), 50 parts by weight of polybutadiene modified polystyrene, 15.0 parts by weight of an etherimide of Example 2, having the formula

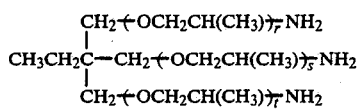

wherein R is

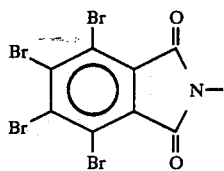

0.15 part by weight of each of zinc sulfide and zinc oxide, and 3.24 parts by weight of antimony oxide. The above components are blended in a Waring blender and extruded in a 28 mm Werner Pfleiderer extruder at 600° F. stock temperature at atmospheric pressure vacuum. The extruded pellets are then molded into standard test bars on a four ounce Newberry injection molding machine (nozzle, front, rear all 505° F., mold, 150° F.). The composition is tested for various properties in accordance with recognized test procedures and the results are shown in Table 1 (which follows Comparative Examples 8–13).

EXAMPLE 7

The procedure of Example 6 is followed using the same starting materials except that a urea of Example 4 having the formula

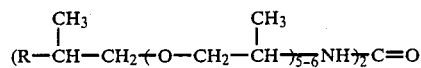

wherein R is tetrabromophthalimido is used in place of the etherimide of Example 2 and the amount of antimony oxide is decreased to 2.45 parts by weight. The results are shown in Table 1 (which follows Comparative Examples 8–13). As shown in Table 1, Examples 6 and 7 of the present invention exhibit excellent flame retardant charactertistics and, further, demonstrate superior tensile and flexural strength.

COMPARATIVE EXAMPLES 8–13

For comparison purposes, six compositions are prepared in the same manner as in Examples 6 and 7 except that the following flame retardant agents were used in place of the etherimide compounds employed in Examples 6 and 7.

COMPARATIVE EXAMPLE 8

4.5 parts by weight of poly(dibromostyrene) homopolymer made by the Great Lakes Corporation; and 1.44 parts by weight of antimony oxide.

COMPARATIVE EXAMPLE 9

10.7 parts by weight of poly(dibromostyrene); and 3.24 parts by weight of antimony oxide.

COMPARATIVE EXAMPLE 10

7.5 parts by weight of poly(dibromostyrene); and 2.45 parts by weight of antimony oxide.

COMPARATIVE EXAMPLE 11

15.0 parts by weight of isopropylated triphenyl phosphate sold by FMC Corporation under the trademark KRONITEX 50®.

COMPARATIVE EXAMPLE 12

15.0 parts by weight of a non-flame retardant, state-of-the-art plasticizer which is an oligomer of 1,3 and 1,4 butylene o-phthalate (sold by Nuodex Corporation under the trademark ADMEX 433B®).

COMPARATIVE EXAMPLE 13

No flame-retardant additives.

The compositions were tested for various properties and the results are set forth in Table 1 as follows:

TABLE 1

| COMPARISON OF FLAME RETARDANT POLYPHENYLENE ETHER/POLYSTYRENE COMPOSITIONS | | | | | | | | |
|---|---|---|---|---|---|---|---|---|
| EXAMPLE | 6 | 7* | 8* | 9* | 10* | 11** | 12* | 13* |
| Composition (Parts by Weight) | | | | | | | | |
| Poly (2,6-dimethyl-1,4-phenylene ether) | 50 | 50 | 50 | 50 | 50 | 50 | 50 | 50 |
| Rubber Modified High Impact Polystyrene[a] | 50 | 50 | 50 | 50 | 50 | 50 | 50 | 50 |
| Flame Retardant Additive | | | | | | | | |
| Example 2 | 15 | — | — | — | — | — | — | — |
| Example 3 | — | 15 | — | — | — | — | — | — |
| KRONITEX 50 | — | — | — | — | — | — | 15 | — |
| ADMEX 433B | — | — | — | — | — | — | — | 15 |
| CN 348L | — | — | 4.5 | 10.7 | 7.5 | — | — | — |
| Antimony Oxide | 3.24 | 2.45 | 1.4 | 3.24 | 2.45 | — | — | — |

TABLE 1-continued

COMPARISON OF FLAME RETARDANT POLYPHENYLENE ETHER/POLYSTYRENE COMPOSITIONS

| EXAMPLE | 6 | 7* | 8* | 9* | 10* | 11** | 12* | 13* |
|---|---|---|---|---|---|---|---|---|
| Stabilizers (ZnS/ZnO) | 0.3 | 0.3 | 0.3 | 0.3 | 0.3 | 0.3 | 0.3 | 0.3 |
| % Bromine | 6.5 | 4.9 | 2.9 | 6.5 | 4.9 | — | — | — |
| Properties | | | | | | | | |
| Flow Channel, inches | 11.5 | 15 | 7 | 8.5 | 7.5 | 8.5 | 19 | 17.5 |
| Heat Distortion temp, °F. | 213 | 214 | 234 | 250 | 250 | 242 | 178 | 177 |
| Notched Izod Input, ft-lbs/in. notch | 2.4 | 2.2 | 4.0 | 3.8 | 3.8 | 3.8 | 3.5 | 3.3 |
| Dynatup Impact, in-lbs. | 176 | 160 | 282 | 264 | 228 | 242 | 232 | 208 |
| Tensile yield strength, psi | 9100 | 8800 | 8800 | 8500 | 8600 | 8500 | 6500 | 7000 |
| Tensile elongation, % | 16 | 17 | 24 | 25 | 25 | 22 | 40 | 50 |
| Flexural modulus, psi | 372,000 | 348,000 | 361,000 | 369,000 | 369,000 | 351,000 | 336,000 | 337,000 |
| Flexural strength, psi | 12,300 | 11,800 | 11,700 | 12,000 | 11,800 | 11,500 | 9,400 | 9,700 |
| Flammability UL 94 rating, 1/16 in., seconds | V-O,3.6 | V-O,3.6 | Fails | V-O,2.0 | V-O,3.6 | Fails | V-O,4.1 | Fails |

*Comparison,
**Control
$^a$HIPS, American Hoechst Co.

As can readily be seen in Table 1, the novel flame retardant agents of the present invention compare favorably in tensile strength and flexural strength properties with the state-of-the-art flame retardant agents. As previously indicated, the flame retardant agents of the present invention are more compatible with thermoplastic resins than brominated flame retardant agents (Comparative Examples 6 versus 9* and 7 versus 10*).

EXAMPLE 14

Poly(1,4-butylene terephthalate)resin, General Electric Co. VALOX® 315), 1550 parts by weight, 440 parts by weight of the flame retardant compound of this invention of Example 3 and 130 parts by weight of antimony oxide were blended and extruded on a 1-¾" Sterling extruder with 450°, 480°,500°, 500° F. set temperatures. The blend was injection molded into test parts and had the following properties:

| | |
|---|---|
| Notched Izod Impact Strength, ⅛" | 0.6 ft. lbs./in. |
| Tensile strength | 6700 psi |
| Tensile elongation | 114% |
| Flammability rating, UL94 | V-O |

Flame retardant compositions according to this invention are also made if the following substitutions are employed:

For the thermoplastic resin, substitute poly(ethylene terephthalate); poly(bisphenol-A carbonate); and an acrylonitrile-butadiene-styrene (ABS) terpolymer; or a poly(2,6-dimethyl-1,4-phenylene-co-2,3,6-trimethyl-1,4-phenylene ether) resin.

To the composition of Example 6, add fibrous glass reinforcement in an amount sufficient to provide 30 parts by weight of glass per 100 parts by weight of glass, polyphenylene ether and high impact rubber modified polystyrene.

In the compositions of Examples 6 and 7, for antimony oxide, substitute stoichiometrical amounts of triphenyl antimony, sodium antimonite and Sb(OCH$_2$CH$_3$)$_3$.

In the embodiments disclosed herein, the compositions comprising polyphenylene ethers or mixtures thereof with styrene resins can be made following the teachings in Hay, U.S. Pat. Nos. 3,306,874 and 3,306,875 and Cizek, U.S. Pat. No. 3,383,435. Particularly preferred compositions comprise from 25 to 75 parts by weight of a polyphenylene ether in combination with 75 to 25 parts by weight of a styrene resin.

The styrene resin is one having at least 25 percent by weight, polymer units derived from the compound having the formula:

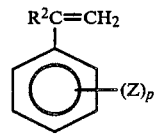

where $R^2$ is hydrogen, (lower)alkyl or halogen; Z is a member selected from the class consisting of vinyl, hydrogen, chlorine and (lower)alkyl; and p is a whole number equal to from 0 to 5. The term "styrene resin" as used throughout this disclosure and in the claims, and defined by the above formula includes by way of example, homopolymers such as polystyrene, the modified polystyrenes such as rubber modified polystyrenes, and the styrene containing copolymers such as the styrene-acrylonitrile copolymers (SAN), styrenebutadiene copolymers, styrene-acrylonitrile-alpha-alkyl styrene copolymers, styrene-acrylonitrilebutadiene copolymers (ABS), poly-alpha-methylstyrene, copolymers of ethylvinylbenzene and divinylbenzene, and the like. The preferred styrene resins are the high impact polystyrenes, the ABS copolymers and the SAN copolymers.

The above-mentioned patents and publications are incorporated herein by reference.

Although the above examples have shown various modifications of the present invention, other variations are possible in the light of the above teachings. It is therefore to be understood that changes may be made in the particular embodiments of the invention described which are within the full intended scope of the invention as defined by the appended claims.

We claim:

1. A flame retardant compound comprising a polyalkylene oxide or derivative thereof end-capped with brominated phthalimide groups and being of the formulae

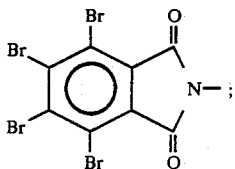

$R^1$ is alkylene of from about 2 to about 6 carbon atoms, $R^2$ is alkyl of from about 1 to about 6 carbon atoms; n is from about 4 to about 40; and n' is from about 3 to about 15 and n" is from about 1 to about 10.

2. The compound of claim 1 of formula (I) wherein n is from about 5 to about 33.

3. The compound of claim 1 of formula (II) wherein n' is from about 4 to about 8.

4. The compound of claim 1 of formula (III) wherein n" is from about 1.5 to about 2.5.

5. The compound of claim 1 wherein $R^1$ is ethylene or propylene.

6. The compound of claim 5 wherein $R^1$ is a

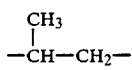

group.

7. The compound of claim 6, wherein said compound is selected from

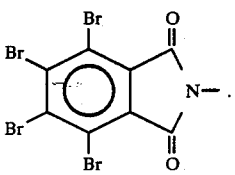

8. A flame retardant compound as described in claim 1 having a molecular weight of from about 400 to about 2,000.

9. A flame retardant compound as described in claim 1 having a melting point of less than about 200° C.

10. A flame retardant compound as described in claim 9 having a melting point of from about 80° C. to about 146° C.

11. A flame retardant compound as described in claim 1 having from about 5 to about 55% by weight of bromine.

12. A flame retardant compound as described in claim 11 having a bromine content of from about 22 to about 53% by weight.

13. The compound of claim 1 comprised of tetrabromophthalic anhydride and polyoxypropylene diamine.

14. The compound of claim 13 wherein the polyoxypropylene has a molecular weight of about 2,000.

15. The compound of claim 14 which has a bromine content of about 22 percent by weight.

16. The compound of claim 13 wherein the polyoxypropylene diamine has a molecular weight of about 400.

17. The compound of claim 16 which has a bromine content of about 50% by weight.

18. The compound of claim 1 comprised of tetrabromophthalic anhydride and polyoxyethylene diamine.

19. The compound of claim 18 wherein the polyoxyethylene has a molecular weight of about 900.

20. The compound of claim 19 which has a bromine content of about 35% by weight.

21. The compound of claim 1 comprised of tetrabromophthalic anhydride and di(aminopolyoxypropylene) urea.

22. The compound of claim 21 wherein the di(aminopolyoxypropylene) urea has a molecular weight of about 700.

23. The compound of claim 22 which has a bromine content of about 37% by weight.

24. The compound of claim 1 comprised of tetrabromophthalic anhydride and polyoxypropylene triamine.

25. The compound of claim 24 in which the polyoxypropylene triamine has the general formula

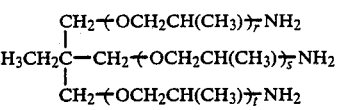

26. The compound of claim 25 wherein the polyoxypropylene triamine has a molecular weight of about 440.

27. The compound of claim 26 which has a bromine content of about 53% by weight.

28. The compound of claim 25 wherein r+s+t is about 5.3.

29. The compound of claim 1 which has a melting point temperature of less than about 200° C.

30. The compound of claim 1 which has a melting point temperature of less than about 146° C.

31. The compound of claim 1 which has a melting point temperature of less than about 125° C.

32. The compound of claim 1 which has a melting point temperature from about 80° C. to about 200° C.

33. The compound of claim 1 which has a bromine content of less than about 55%.

34. The compound of claim 1 which has a bromine content of less than about 37%.

35. The compound of claim 1 which has a bromine content of less than about 35%.

36. The compound of claim 1 which has a bromine content of less than about 22%.

* * * * *